US007695976B2

(12) United States Patent
Kim et al.

(10) Patent No.: US 7,695,976 B2
(45) Date of Patent: Apr. 13, 2010

(54) METHOD FOR UNIFORM ANALYTE FLUID DELIVERY TO MICROARRAYS

(75) Inventors: Gibum Kim, Bothell, WA (US); R. Todd Schwoerer, Edmonds, WA (US)

(73) Assignee: Plexera Bioscience, LLC, Bothell, WA (US)

( * ) Notice: Subject to any disclaimer, the term of this patent is extended or adjusted under 35 U.S.C. 154(b) by 360 days.

(21) Appl. No.: 11/846,908

(22) Filed: Aug. 29, 2007

(65) Prior Publication Data

US 2009/0060787 A1 Mar. 5, 2009

(51) Int. Cl.
*G01N 33/00* (2006.01)

(52) U.S. Cl. ........................ 436/180; 422/58; 422/68.1; 422/100; 422/102

(58) Field of Classification Search ....................... None
See application file for complete search history.

(56) References Cited

U.S. PATENT DOCUMENTS

| | | | | |
|---|---|---|---|---|
| 6,165,335 | A | 12/2000 | Lennox et al. | |
| 6,461,490 | B1 | 10/2002 | Lennox et al. | |
| 6,478,939 | B1 | 11/2002 | Lennox et al. | |
| 6,776,965 | B2 * | 8/2004 | Wyzgol et al. | 422/100 |
| 6,862,094 | B2 | 3/2005 | Johansen | |
| 6,999,175 | B2 | 2/2006 | Ivarsson | |
| 7,084,980 | B2 | 8/2006 | Jones et al. | |
| 7,251,085 | B2 | 7/2007 | Bahatt et al. | |
| 7,463,358 | B2 | 12/2008 | Wolf et al. | |
| 2004/0037739 | A1 * | 2/2004 | McNeely et al. | 422/58 |
| 2004/0258832 | A1 | 12/2004 | Barklund et al. | |
| 2004/0265171 | A1 * | 12/2004 | Pugia et al. | 422/58 |
| 2005/0014179 | A1 | 1/2005 | Karlsson et al. | |
| 2005/0200845 | A1 | 9/2005 | Nabatova-Gabain et al. | |
| 2005/0229696 | A1 * | 10/2005 | Takayama | 73/204.26 |
| 2006/0134669 | A1 | 6/2006 | Casasanta | |
| 2006/0234265 | A1 | 10/2006 | Richey et al. | |
| 2007/0004029 | A1 * | 1/2007 | Aoyagi | 435/287.2 |
| 2007/0059817 | A1 * | 3/2007 | Aoyagi | 435/287.2 |
| 2007/0081163 | A1 | 4/2007 | Liang et al. | |
| 2007/0139653 | A1 | 6/2007 | Guan et al. | |
| 2007/0222996 | A1 | 9/2007 | Guan et al. | |
| 2009/0060786 | A1 | 3/2009 | Kim et al. | |
| 2009/0060787 | A1 | 3/2009 | Kim et al. | |

OTHER PUBLICATIONS

Kim et al.; U.S. Appl. No. 12/339,017, filed Dec. 18, 2008.

* cited by examiner

*Primary Examiner*—Krishnan S Menon
*Assistant Examiner*—Dirk Bass
(74) *Attorney, Agent, or Firm*—Graybeal Jackson LLP

(57) ABSTRACT

A method of chemical analysis that includes: a) introducing an analyte fluid having a flow to a surface of a sample chip through a microfluidic device comprising i) a fluid inlet having a semi-circular groove and ii) a flow chamber comprising an inner wall having an inlet end, where the fluid inlet is in communication with the flow chamber and where the inner wall at the inlet end is curved and has a radius similar to the radius of semi-circular groove; b) maintaining the flow of the analyte fluid such that the analyte fluid forms a pattern on the surface of the sample chip, the pattern approximating the semi-circular groove; c) maintaining the flow of the analyte fluid so that a linear fluid front forms on the surface of the sample chip at the inlet end; and d) maintaining the flow so that the linear fluid front moves along the surface of the sample chip.

18 Claims, 4 Drawing Sheets

METHOD FOR UNIFORM ANALYTE FLUID DELIVERY TO MICROARRAYS

BACKGROUND

Microfluidic flow cells that are used in, for example, microarray chemical analysis typically have small holes for fluid inlet and outlet. When the microarray area covers a large area, such as in high throughput analysis, the flow becomes localized between the fluid inlet and outlet, which results in high non-uniformity of the analyte across the surface of the microarray. To help alleviate this problem, a higher flow rate for the analyte fluid may be used to exchange the fluid in the flow cell; however, such high flow rates are undesirable because the analyte is often precious and may be present at low concentration.

SUMMARY

One embodiment is a microfluidic device that comprises: a) a fluid inlet having a semi-circular groove and b) a flow chamber having an inlet end, wherein the fluid inlet and flow chamber are in communication and wherein the inner wall at the inlet end is curved with a radius similar to the radius of the semi-circular groove. An analyte fluid introduced through the groove flows across the surface of a microarray with high uniformity and does not require high analyte fluid volumes to exchange the fluid in the flow cell. The flow chamber may be in communication with a sample chip. In some embodiments, fluid flows through the flow chamber and is contained between a) the bottom surface adjacent to the fluid inlet and b) the surface of the sample chip. The surface of the sample chip may have an analysis area to which is immobilized, for example, probe molecules such as peptides, proteins, DNA, RNA, etc. In another embodiment the microfluidic device further comprises a fluid outlet end having a fluid outlet, wherein the inner wall of the flow chamber at the outlet end tapers toward the fluid outlet. Another embodiment is an assembly for chemical analysis comprising any of the microfluidic devices as described above and the sample chip having a surface comprising an analysis area, wherein the surface is in communication with the flow chamber.

Another embodiment is a method of chemical analysis comprising: a) introducing an analyte fluid having a flow to the surface of a sample chip through a microfluidic device comprising i) a fluid inlet having a semi-circular groove and ii) a flow chamber having an inlet end, wherein the fluid inlet is in communication with the flow chamber and wherein the inner wall at the inlet end is curved with a radius similar to the radius of the semi-circular groove; b) maintaining the flow of the analyte fluid such that the analyte fluid forms a pattern on the surface of the sample chip, the pattern approximating the semi-circular groove; c) maintaining the flow of the analyte fluid so that a linear fluid front forms on the surface of the sample chip at the inlet end; and d) maintaining the flow so that the linear fluid front moves along the surface of the sample chip.

DETAILED DESCRIPTION

Figure 1:
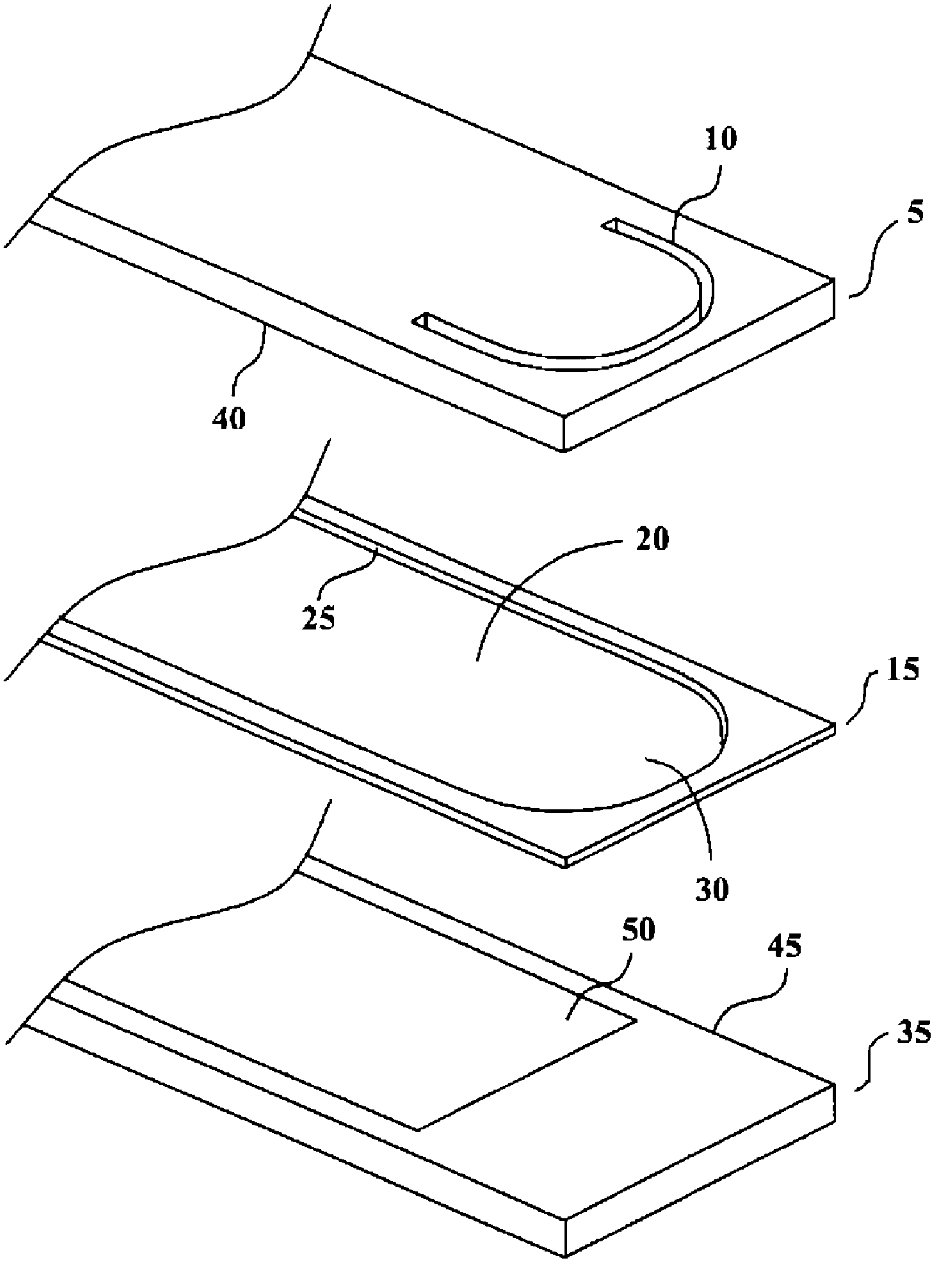
FIG. 1 illustrates one view of the microfluidic device.
Figure 2A:
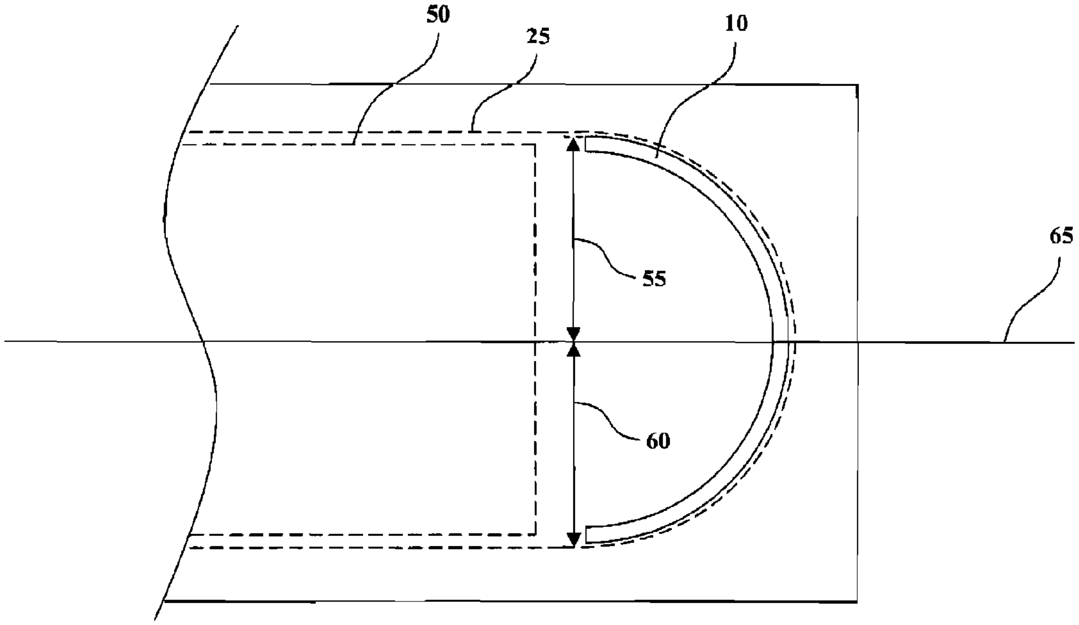
FIG. 2*a* illustrates a top down view relative to FIG. 1 of the microfluidic device.
Figure 2B:
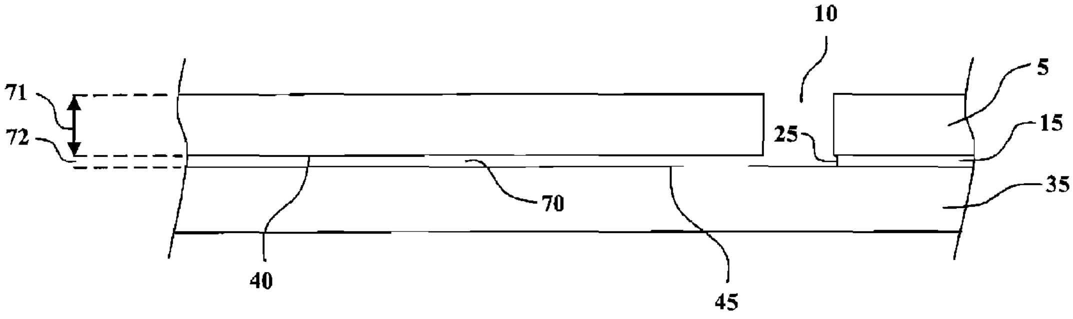
FIG. 2*b* illustrated a cross section of the microfluidic device
Figure 3:
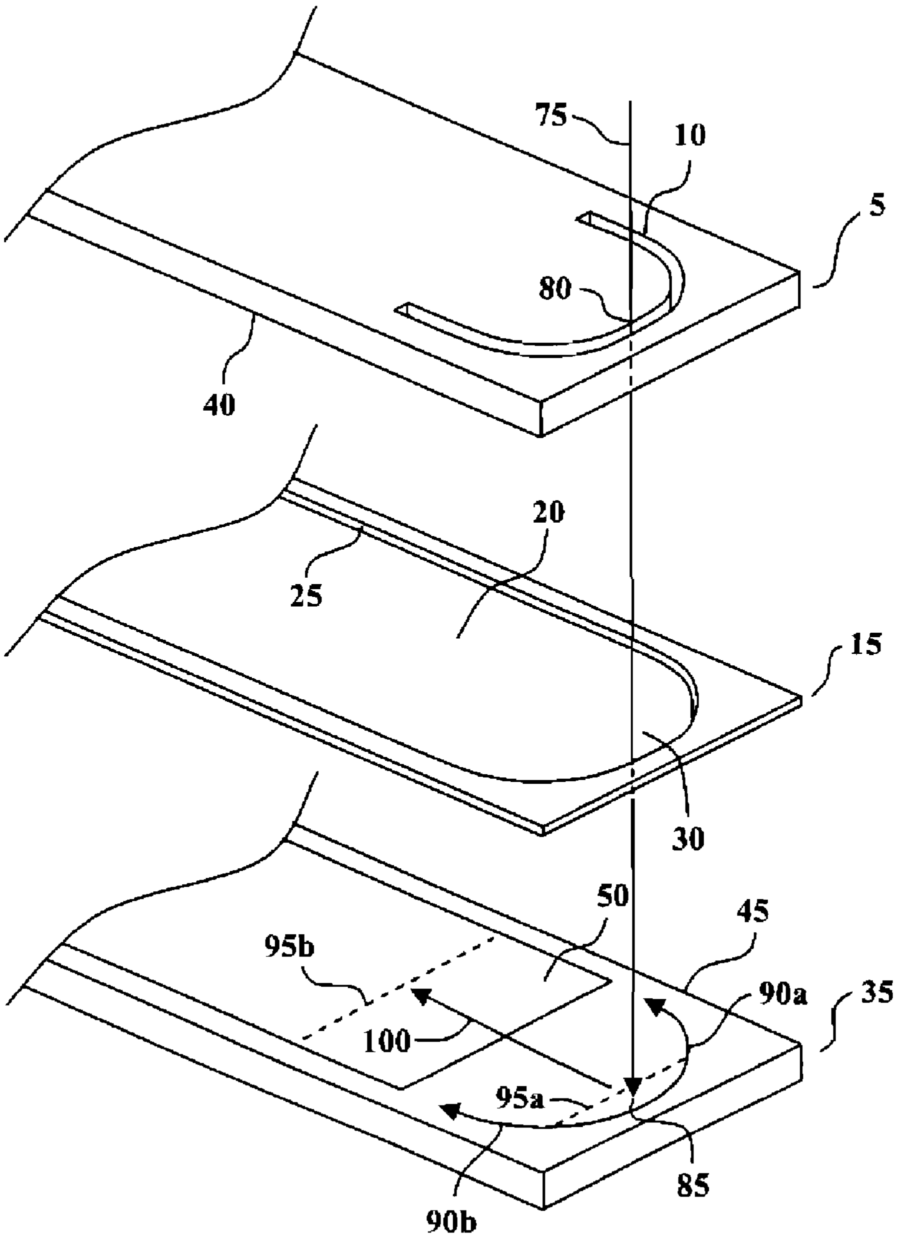
FIG. 3 illustrates the fluid flow through the microfluidic device

One embodiment, referring to FIG. 1, is a microfluidic device that comprises: a) a fluid inlet 10 having a semi-circular groove and b) a flow chamber 20 comprising an inner wall 25 having an inlet end 30, wherein fluid inlet 10 is in communication with flow chamber 20 and wherein inner wall 25 at inlet end 30 is curved with a radius similar to the radius of the semi-circular groove. Flow chamber 20 may be in communication with a sample chip 35. In some embodiments, fluid flows through flow chamber 20 and is contained between bottom surface 40 and surface 45 of sample chip 35. Surface 45 of sample chip 35 may have analysis area 50 to which is immobilized, for example, probe molecules, peptides, proteins, DNA, RNA, etc. FIG. 2*a* illustrates the microfluidic device from a "top down" view relative to FIG. 1. FIG. 2*a* shows fluid inlet 10 having a semi-circular groove, the outline of analysis area 50, the outline of inner wall 25, the radius 55 of the fluid inlet 10 having a semi-circular groove, and radius 60 of inner wall 25 at inlet end 30. FIG. 2*b* illustrates a cross section view of the microfluidic device along plane 65 (FIG. 2*a*). FIG. 2*b* shows the cross section of the fluid inlet 10 having a semi-circular groove, flow chamber 20, inner wall 25, sample chip 35, and space 70 where the a fluid in contained between bottom surface 40 and surface 45 of sample chip 35. FIG. 3 illustrates a method of operating the microfluidic device by introducing a fluid flow 75 at roughly the middle 80 of fluid inlet 10 having a semi-circular groove. The fluid flow passes through flow chamber 20 at inlet end 30 and contacts surface 45 of sample chip 35. From the point of contact 85 with surface 45 of sample chip 35, the fluid flows outward 90*a*, 90*b* in a pattern that approximates semi-circular groove. When the fluid fills up the semi-circular groove, a linear front begins forming 95*a* at point of contact 85 and then flows 100 along surface 45 of sample chip 35 with the linear front 95*b* maintained. The flow of fluid through flow chamber 20 is highly uniform across the relatively large surface area of a sample chip.

It should be noted that in the FIGS. 1-4 fluid inlet 10 is shown in a separate layer 5 and flow chamber 20 is shown in a separate layer 15. However, fluid inlet 10 and flow chamber 20 need not be in separate layers. In some embodiments, fluid inlet 10 and flow chamber 20 comprise separate layers (e.g., layer 5 and layer 15, respectively). These layers can be, for example, pressure sensitive adhesive tape, or other material such as teflon, having a variety of thicknesses. In other embodiments, fluid inlet 10 and flow chamber 20 comprise a single layer and may be, for example, fabricated as one solid piece. Such embodiments may have fluid inlet 10 and flow chamber 20 fabricated sequentially or concurrently by, for example, techniques that include machining of a solid block material, embossing a material, molded UV curing, molded thermosetting, etc. and any combination thereof. Materials that the layers can be made from include plastics such as, for example Lucite or Teflon, metals and alloys, and glass or silicon. Bottom surface 40, the inner walls of fluid inlet 10, and/or inner wall 25 of flow chamber 20 may have additional structures protruding into or receding from the fluid path in order to, for example, enhance mixing or improve general flow dynamics.

In various embodiments, the microfluidic device may have one or more of the following features. Radius 60 of inner wall 25 is from about 105% to about 107% larger than radius 55 of the semi-circular groove. The width of the groove is from about 350 micron to about 500 micron and radius 55 of the semi-circular groove is from about 3.5 cm to about 4 cm. The depth 71 of fluid inlet 10 is from about 25 microns to about 40 microns. The depth 72 of flow chamber 20 is from about 13 microns to about 20 microns.

Figure 4:
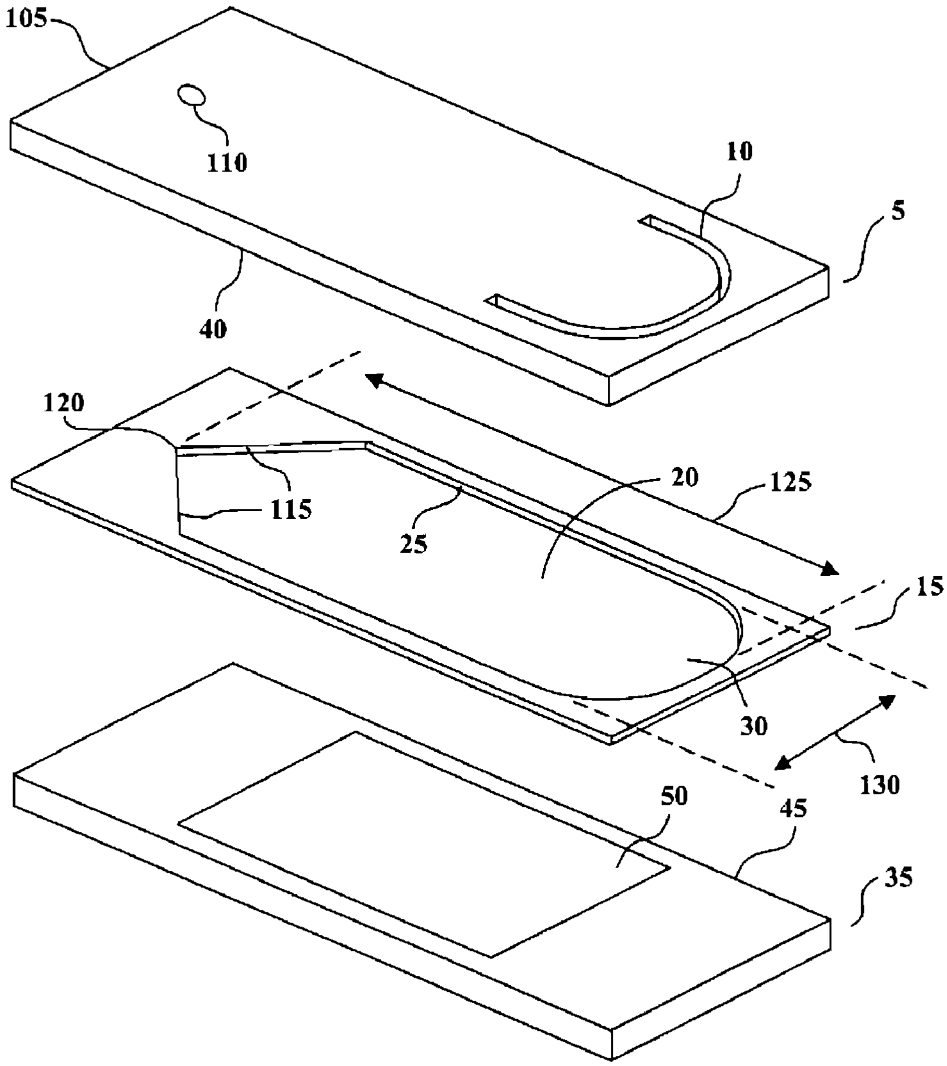
FIG. 4 illustrates one embodiment of the microfluidic device.

In another embodiment, referring to FIG. 4, the microfluidic device further comprises a fluid outlet end 105 having a fluid outlet 110, wherein inner wall 25 of flow chamber 20 at outlet end 105 tapers (115) toward fluid outlet 110. Apex 120 of the taper is allows fluid to flow through fluid outlet 110 and out of flow chamber 20. In various embodiments, the invention may include one or more of the following. The length 125 of flow chamber 20 may be from about 3 cm to about 4.5 cm and the width 130 of flow chamber 20 may be about 1.4 cm to about 1.6 cm. The volume of flow chamber 20 is from about 6 μL to about 10 μL. The microfluidic device has a fluid exchange volume between about 80% and about 130% of the volume of flow chamber 20. In one embodiment, the depth 71 of fluid inlet 10 is about 13 microns to about 20 microns, semi-circular groove has a width of about 350 micron to about 500 micron and radius 55 of about 3.5 cm to about 4 cm, the depth 72 of flow chamber 20 is about 13 microns to about 20 microns, and flow chamber 20 has length 125 of about 3 cm to 4.5 cm and width 130 of about 1.4 cm to about 1.6 cm.

Another embodiment is an assembly for chemical analysis comprising any of the microfluidic devices as described above and sample chip 35 having surface 45 comprising analysis area 50, wherein surface 45 is in communication with flow chamber 20. Various embodiments may have one or more of the following features. Analysis area 50 is at least 1.5 sq. cm. Analysis area 50 includes a microarray comprising analysis spots. At least one analysis spot of the microarray may comprise a biomolecule. The biomolecule may be a polypeptide or a polynucleotide. The microarray may also comprise a plurality of polypeptides, polynucleotides, or both.

Another embodiment, referring to FIGS. 1-4, is a method of chemical analysis comprising: a) introducing an analyte fluid having a flow to surface 45 of sample chip 35 through a microfluidic device comprising i) a fluid inlet 10 having a semi-circular groove for fluid inlet and ii) a flow chamber 20 comprising an inner wall 25 having an inlet end 30, wherein the fluid inlet 10 is in communication with flow chamber 20 and wherein inner wall 25 at inlet end 30 is curved with a radius similar to the radius of the semi-circular groove; b) maintaining the flow of the analyte fluid such that the analyte fluid forms a pattern on surface 45 of the sample chip 35, the pattern approximating the semi-circular groove; c) maintaining the flow of the analyte fluid so that linear fluid front 95*a* forms on surface 45 of sample chip 35 at inlet end 30; and d) maintaining the flow so that a linear fluid front 95*b* moves along surface 45 of sample chip 35. The various features of the microfluidic device may include those described above and illustrated in FIGS. 1-4. Embodiments may have one or more of the following features. The flow has a rate of about 180 μL/min to about 600 μL/min and a pressure of about 5 to about 30 PSI. Surface 45 of sample chip 35 comprises analysis area 50 that is at least 1.5 sq. cm. Analysis area 50 includes a microarray comprising analysis spots. At least one analysis spot comprises a biomolecule. The biomolecule is a polypeptide or a polynucleotide. The microarray comprises a plurality of polypeptides, polynucleotides, or both.

Other embodiments are within the following claims.

The invention claimed is:

1. A method of chemical analysis comprising: a) introducing an analyte fluid having a flow to a surface of a sample chip through a microfluidic device comprising i) a fluid inlet having a semi-circular groove and ii) a flow chamber comprising an inner wall having an inlet end, wherein the fluid inlet is in communication with the flow chamber and wherein the inner wall at the inlet end is curved and has a radius similar to the radius of semi-circular groove; b) maintaining the flow of the analyte fluid such that the analyte fluid forms a pattern on the surface of the sample chip, the pattern approximating the semi-circular groove; c) maintaining the flow of the analyte fluid so that a linear fluid front forms on the surface of the sample chip at the inlet end; and d) maintaining the flow so that the linear fluid front moves along the surface of the sample chip.

2. The method of claim 1, wherein the fluid inlet and the flow chamber comprise separate layers.

3. The method of claim 1, wherein the fluid inlet and the flow chamber comprise a single layer.

4. The method of claim 1, wherein the radius of the inner wall is from about 105% to about 107% larger than the radius of the groove.

5. The method of claim 1, wherein the width of the groove is from about 350 micron to about 500 micron and the radius of the groove is from about 1.8 cm to about 2 cm.

6. The method of claim 1, wherein the depth of the fluid inlet is from about 20 microns to about 40 microns.

7. The method of claim 1, wherein the depth of the flow chamber is from about 13 microns to about 20 microns.

8. The method of claim 1, further comprising a fluid outlet end having a fluid outlet, wherein the inner wall at the outlet end tapers toward the fluid outlet.

9. The method of claim 8, wherein the length of the flow chamber is from about 4 cm to about 4.5 cm and the width of the flow chamber is about 1.4 cm to about 1.6 cm.

10. The method of claim 9, wherein the volume of the flow chamber is from about 6 μL to about 10 μL.

11. The method of claim 10, wherein the flow chamber has a fluid exchange volume between about 80% and about 130% of the flow chamber volume.

12. The method of claim 8, wherein the depth of the fluid inlet is about 20 microns to about 40 microns, the semi-circular groove has a width of about 350 micron to about 500 micron and a radius of about 3.5 mm to about 4 mm, the depth of the flow chamber is about 13 microns to about 20 microns, and the flow chamber has a length of about 3.5 cm to 4 cm and a width of about 1.4 cm to about 1.6 cm.

13. The method of claim 8, wherein the flow has a rate of about 180 μL/min to about 600 μL/min and a pressure of about 5 to about 30 PSI.

14. The method of claim 1, wherein the surface of the sample chip comprises an analysis area that is at least 1.5 sq. cm.

15. The method of claim 14, wherein analysis area is a microarray comprising analysis spots.

16. The method of claim 15, wherein at least one analysis spot comprises a biomolecule.

17. The method of claim 16, wherein the biomolecule is a polypeptide or a polynucleotide.

18. The method claim 15, wherein the microarray comprises a plurality of polypeptides, polynucleotides, or both.

* * * * *